United States Patent

Züchner et al.

[11] Patent Number: 5,777,206
[45] Date of Patent: Jul. 7, 1998

[54] METHOD AND MEASURING DEVICE FOR DETERMINING THE WATER CONTENT OF A GAS

[76] Inventors: Klaus Züchner, Angerstrasse 12 a., D-37073 Göttingen, Germany; Thomas Schulze, Sackstrasse 13., D-37191 Katlenburg, Germany; Gerrit Kahle, Bramwaldstrasse 6., D-37081 Göttingen, Germany

[21] Appl. No.: 776,929
[22] PCT Filed: Jun. 26, 1996
[86] PCT No.: PCT/DE96/01163
  § 371 Date: Feb. 26, 1997
  § 102(e) Date: Feb. 26, 1997
[87] PCT Pub. No.: WO97/02486
  PCT Pub. Date: Jan. 23, 1997

[30] Foreign Application Priority Data

Jun. 30, 1995 [DE] Germany ............ 195 23 601.7

[51] Int. Cl.$^6$ ............ G01W 1/00; G01N 25/64; H01L 7/00
[52] U.S. Cl. ............ 73/29.01; 73/73; 73/335.04; 324/674; 324/689; 338/34; 338/314; 422/83; 422/98
[58] Field of Search ............ 73/29.01, 29.02, 73/336.5, 335.01, 335.03, 335.05, 335.04, 73; 338/34, 35, 314; 361/286; 324/674, 676, 678, 689; 422/83, 98

[56] References Cited

U.S. PATENT DOCUMENTS

| | | | |
|---|---|---|---|
| 3,945,217 | 3/1976 | Bashark | 62/151 |
| 4,017,820 | 4/1977 | Ross | 338/35 |
| 4,164,868 | 8/1979 | Suntola | 73/336.5 |
| 4,563,634 | 1/1986 | Lehle | 324/61 R |
| 4,564,882 | 1/1986 | Baxter et al. | 361/286 |
| 4,580,354 | 4/1986 | Lindberg | 34/26 |
| 4,875,990 | 10/1989 | Kodachi et al. | 204/408 |
| 4,975,249 | 12/1990 | Elliott | 422/83 |
| 5,296,819 | 3/1994 | Kuroiwa et al. | |
| 5,317,274 | 5/1994 | Nakagawa et al. | 324/678 |
| 5,345,810 | 9/1994 | Rosen | 73/29.02 |
| 5,418,131 | 5/1995 | Butts | 435/3 |

FOREIGN PATENT DOCUMENTS

| | | |
|---|---|---|
| 48229 | 1/1974 | Finland . |
| 19513274 | 11/1995 | Germany . |
| 1158340 | 6/1989 | Japan . |

*Primary Examiner*—Hezron E. Williams
*Assistant Examiner*—J. David Wiggins
*Attorney, Agent, or Firm*—Burns, Doane, Swecker & Mathis, L.L.P.

[57] ABSTRACT

The invention concerns a method and measuring device for determining the water content of a gas. The measuring device comprises a measuring sensor arrangement which consists of: a capacitive sensor thermally coupled to a heating element and to a temperature sensor; an energy source connected to the heating element; a first evaluation circuit connected to the temperature sensor. The heating element and the temperature sensor are formed by a common temperature-dependent resistor. Together with the temperature dependent resistor and the energy source, the second evaluation circuit forms a control circuit for keeping the temperature of the capacitive sensor constant. As a function of the capacity of the capacitive sensor as the sole variable the first evaluation circuit determines the actual value of the relative humidity of the gas from previously determined calibrating values at the same constant temperature by interpolation or extrapolation of the calibrating values.

20 Claims, 2 Drawing Sheets

METHOD AND MEASURING DEVICE FOR DETERMINING THE WATER CONTENT OF A GAS

FIELD OF THE INVENTION

The present invention concerns both an instrument for determining the water content of a gas and a method of determining the water content of a gas.

BACKGROUND OF THE INVENTION

A method of measuring condensation point or gas concentration and a device for predicting ice formation are known from German 19 513 274 A1. The known method and device also allow determination of relative and absolute humidity.

The humidity sensor is a capacitive sensor heated by a heating element to a point of maximal sensitivity. This is the point in the particular embodiment where the relative humidity is between 60 and 80%. Relative humidity is then determined by processing two variables, specifically the relative humidity determined by the sensor at operating temperature and the temperature of the sensor itself as determined by a separate temperature probe.

SUMMARY OF THE INVENTION

The object of the present invention is an instrument for and a method of determining the water content of a gas that will allow the determination of humidity from only one variable and will operate more precisely.

This object is attained in accordance with the present invention in the instrument recited in the preamble to claim 1 and in the method recited in the preamble to claim 9 as recited in the body of each of those claims.

Advanced versions and advantageous embodiments are recited in the subsidiary claims.

The instrument in accordance with the present invention employs a single temperature-dependent resistor instead of a heating element and a separate temperature probe. The resistors temperature dependence is accordingly exploited to detect the actual temperature from the change in resistance that accompanies heating. The temperature can accordingly be determined directly, meaning without the transition loss and delay that occur when heat is transmitted from one component to another. Restricting the procedure to a single common temperature-dependent resistor also allows considerable reduction in the size of the overall instrument, which in turn promotes rapid response to any changes due to low heat capacity. This behavior makes it possible to also employ the instrument as a component of a rapid response regulator that will ensure constant humidity.

Thermal coupling of the capacitive sensor to a resistor that is heated to and maintained at a constant temperature will maintain the sensor as well at the same constant temperature. It will be necessary in interpreting the results to take into consideration only one more variable, specifically changes in capacity as a function of humidity. Interpretation can simultaneously be restricted to the interpolation or extrapolation of values determined from prior calibration at the same temperature. Thus the interaction, reproducible at constant temperatures, between capacity and relative or absolute humidity can be exploited for the interpretation. This reproducible interaction can be expressed by a function that is either linear or nonlinear, depending on the type of sensor employed and on the particular operating temperature. The function will represent a measure of relative or absolute humidity. The other humidity parameter in every case, meaning absolute humidity when relative humidity is determined first or relative humidity when absolute humidity is determined first, can be obtained by known methods from the initial result and the partial pressure of the water vapor.

The instrument preferably includes a flat base of highly heat conductive ceramic with the capacitive sensor on one side and the temperature-dependent resistor on the other.

This feature results in a compact structure, whereby the base itself provides electric insulation between the two components while constituting an extensive heat conductor that couples the temperature of the capacitive sensor tight to that of the resistor.

The instrument can also have a thermal insulation wrap that acts as heat insulation although it is discontinuous and moisture permeable on the side the capacitive sensor is mounted on.

This strategy decreases heat radiation into the environment, allowing the temperature-dependent resistor to be operated at low heat output. The thermal separation from the environment also ensures relatively better coupling between the resistor and the capacitive sensor.

The temperature-dependent resistor in one embodiment of the instrument is accommodated in a measuring bridge. The energy source is a pulse generator connected to the bridge. The input terminal of the signal-processing circuit is connected to the diagonal of the bridge and its output terminal to a regulator that regulates the pulse generator's pulse-to-pause ratio.

The measuring bridge decreases the effect of the absolute value of the voltage supplied to the temperature-dependent resistor. The same is true of the superposed interference voltage. This strategy increases useful sensitivity.

The effective heat output of the temperature-dependent resistor can be controlled more precisely by varying the supply voltage's pulse-to-pause ratio at a comparable expenditure for circuitry over a limit range of regulation than by measuring and controlling absolute value or amplitude.

The temperature-dependent resistor in another embodiment of the instrument is also included in a measuring bridge. The energy source, however, is a source of direct voltage or direct current connected to the bridge. A pulse generator superposes a signal of constant amplitude over the direct voltage or direct current from the energy source. The second signal-processing circuit demodulates the signal from the pulse generator. The second signal-processing circuit's input terminal is connected to the bridge's diagonal and its output terminal to a regulator that controls the direct voltage or direct current from the energy source. This embodiment utilizes an auxiliary voltage that can be separated from the energy source's direct voltage or direct current and accordingly, processed independently of any changes in voltage or current dictated by the regulating conditions. Processing is accordingly uncontaminated and hence more precise.

It is preferable for the first signal-processing circuit to include a pulse generator wherein the capacitive sensor constitutes the timing stage. Either the pulse frequency or the pulse-to-pause ratio is accordingly measured. This approach ensures that the method will be insensitive to contaminating voltages.

Still another signal-processing circuit in one advanced version detects deviations in the performance of the regulator or in heat output, compares them with previously obtained calibration values, and accordingly determines how rapidly the gas is flowing.

The speed of the gas is accordingly measured indirectly by way of the heat of convection, which must of course be compensated for by increasing the heat in order to maintain the requisite constant temperature. The insulation provided by the wrap need not be as powerful in this embodiment in order to permit well defined convection. Since convection also depends to some extent on how humid the gas is, the measurements can be improved in another advanced embodiment by taking relative humidity into consideration.

BRIEF DESCRIPTION OF THE DRAWING FIGURES

The present invention will now be specified with reference to the accompanying drawing, wherein FIG. 1 is a side view of an instrument for determining the water content of a gas, FIG. 2 is a block diagram of a one embodiment of peripherals connected to a temperature-dependent resistor, FIG. 3 is a block diagram of another embodiment of peripherals connected to a temperature-dependent resistor, FIG. 4 is a graph of the voltage that occurs over time in the circuitry illustrated in FIG. 3, and FIG. 5 is a block diagram of the circuitry that processes the signals deriving from the capacitive sensor.

DETAILED DESCRIPTION OF THE INVENTION

Figure 1:
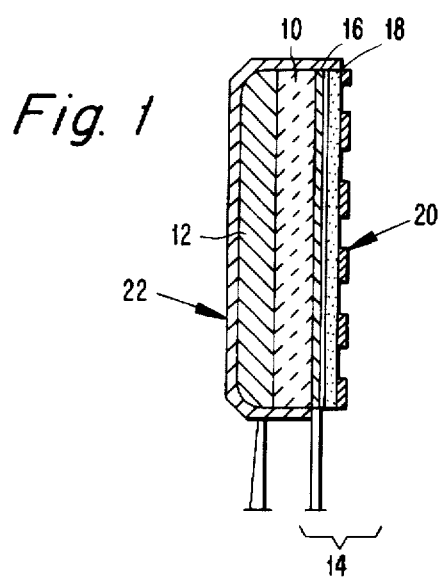

The instrument illustrated in FIG. 1 comprises a flat base 10 of highly heat conductive ceramic with a platinum temperature dependent resistor 12 on one side and a capacitive sensor 14 on the other. An electrode 16 extends through capacitive sensor 14 and fastens directly to base 10. Capacitive sensor 14 also includes a dielectric 18 with a dielectric constant that varies with humidity. Another electrode 20, porous and moisture permeable, is mounted on the capacitive sensor 14. The instrument is wrapped, except for second electrode 20, in a wrap 22. Wrap 22 acts as thermal insulation and decreases heat loss to the environment.

Figure 2:
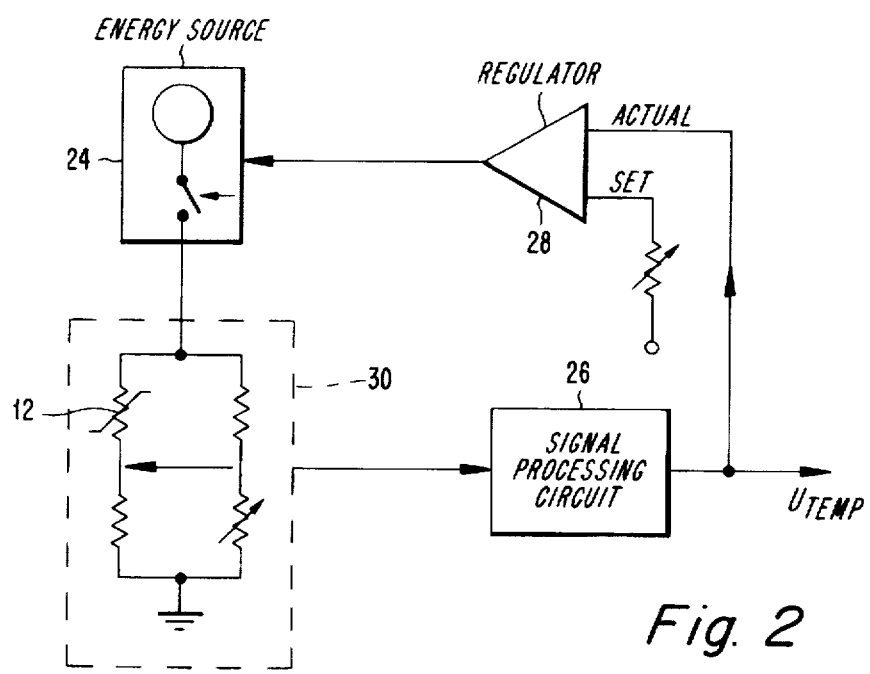

FIG. 2 shows a block diagram of a first embodiment of peripherals connected to temperature dependent resistor. These peripherals include a source 24 of energy, a signal processing circuit 26, and a regulator 28. Temperature dependent resistor 12 is accommodated in a measuring bridge 30. The bridge's bridging branch is connected to the input terminal is supplied with current from energy source 24. The bridge's diagonal is connected to the input terminal of signal processing circuit 26. The bridge's voltage varies in accordance with variations in the resistance of temperature-dependent resistor 12. Signal-processing circuit 26 determines from the bridge's voltage the resistor's 12 actual temperature, which, due to the thermal coupling to capacitative sensor 14, also extensively corresponds to the temperature of the sensor 14.

The output terminal of signal-processing circuit 26 is connected to the input terminal of regulator 28. The output terminal of regulator 28 controls energy source 24. The energy source 24 in this particular embodiment turns on and off, regulating the output of heat by way of the pulse-to-pause ratio of a switched constant voltage. It is alternatively possible for the energy source to be a pulse generator, with a pulse-to-pause ratio controlled by a control stage.

Figure 3:
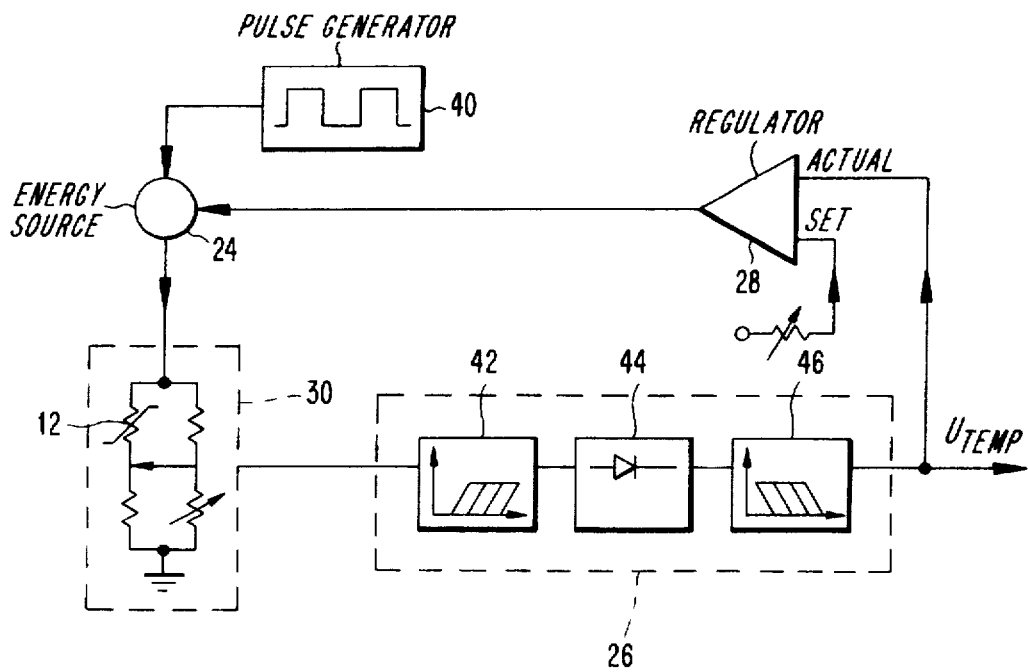
Figure 4:
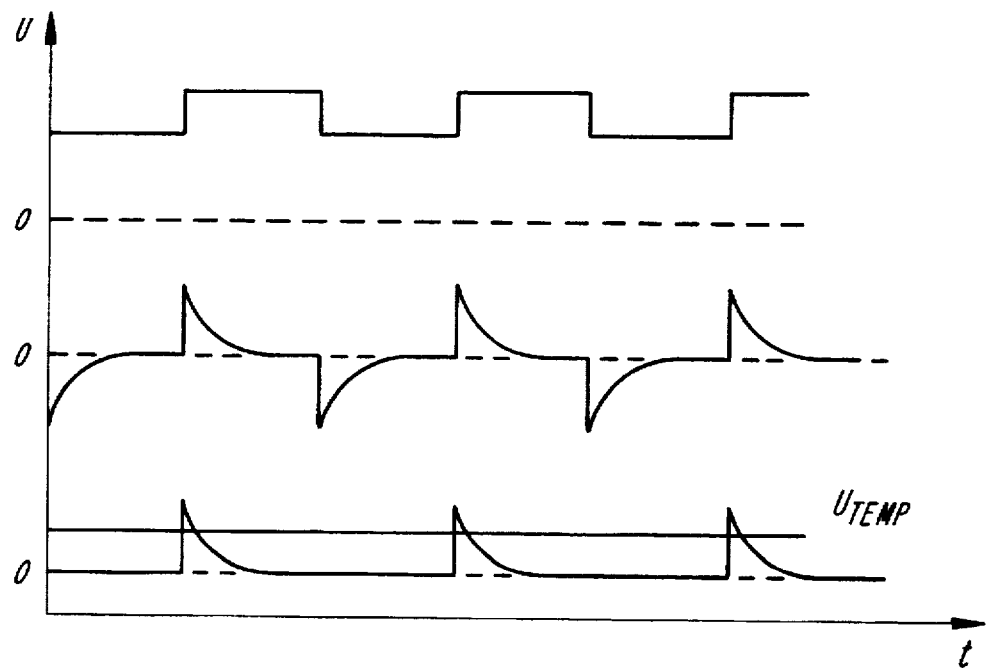

The peripherals illustrated in FIG. 3 are also connected to the temperature-dependent resistor. They differ from the peripherals illustrated in FIG. 2 in that energy source 24 is a source of constant voltage and in that they include a pulse generator 40 that superposes signals of constant amplitude on the constant voltage arriving from the energy source 24. This situation will be evident from the graph of voltage over time in FIG. 4. A voltage composed of a variable constant-voltage component and a constant alternating-voltage component is supplied to measuring bridge 30.

The input terminal of signal-processing circuit 26 is connected to the diagonal of measuring bridge 30. Signal processing circuit 26 demodulates the signal from pulse generator 40. The demodulated signal is just a measure of the temperature of temperature dependent resistor 12 and is independent of the actual level of constant voltage coming from energy source 24. The temperature dependent signal can control by way of regulator 28 the level of the constant voltage from energy source 24 in accordance with a reference level.

The signal-processing circuit 26 in the instant embodiment comprises a high-pass filter 42, a downstream rectifier 44, and a low-pass filter 46. High-pass filter 42 separates the alternating current signal from the constant voltage. What happens to the alternating current leaving low-pass filter 46 will be evident from the middle plot in FIG. 4. The signal leaving rectifier 44 is represented by the pulses in the lower plot in FIG. 4. Low pass filter 46 shapes the pulses arriving from rectifier 44 into the extensively constant "constant-voltage" also illustrated in the lower graph of voltage over time in FIG. 4.

High-frequency interference can be prevented by employing a bandpass instead of high-pass filter 42 and a synchronous demodulator instead of rectifier 44. The synchronous demodulator can be synchronized by pulse generator 40. Signal processing circuit 26 can alternatively be integrated into the overall instrument along with appropriately miniaturized components to improve interference resistance even more. The basal heating that derives from the energy employed to improve resistance measurement can be decreased by reducing the amplitude of the square alternating current employed for measurement.

Figure 5:
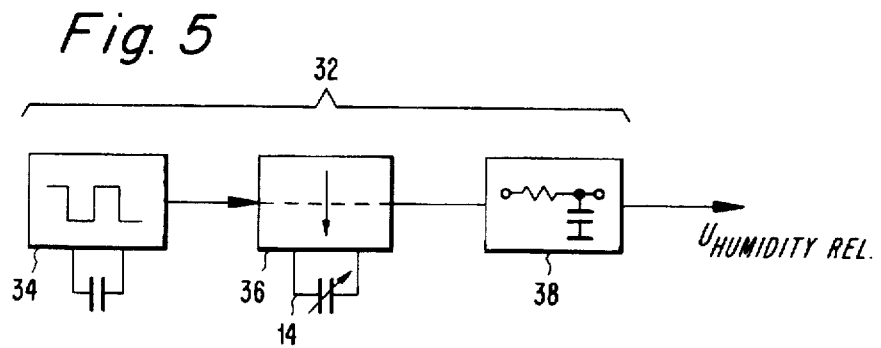

FIG. 5 illustrates a block diagram of the circuit 32 for the capacitative sensor 14. Circuit 32 comprises an astable flip-flop stage 34, a monostable flip-flop stage 36, and a detector 38. Capacitative sensor 14 is integrated into monostable flip-flop stage 36 as a time determining component. Flip-flop stage 34 triggers monostable flip-flop stage 36 at constant intervals. Monostable flip-flop stage 36 returns to a stable state at intervals dictated by capacitative sensor 14, resulting in pulses with a variable pulse-to-pause ratio. Detector 38 can be either a low-pass filter that determines an analog value from the pulse-to-pause ratios or even a digital timer.

Two-point calibration is completely satisfactory for obtaining precision. The instrument is for this purpose heated to operating temperature, and values obtained for low and high humidities. The lower point can be represented by dry air and the upper point by a saturated salt solution.

Depending on the humidities typical of each calibration point, which can if necessary be verified by further measurements, the result associated with the lower point can be assigned to a relative humidity of approximately 0% and the result associated with the upper point to a relative humidity of approximately 90%. The intermediate values can then be established by linear interpolation between the points. In the event of non-linear dependence, additional points of calibration must be established and verified by testing. Operating temperature must always be higher than the condensation point of the particular gas being tested.

When different gases or mixtures of gases are to be tested, the calibration can be gas-specific. Otherwise, the calibration undertaken for a specific gas can be modified with gas-specific correction values.

Absolute humidity can be determined from relative humidity by taking the partial pressure of the water vapor into consideration. This can be done from a table or by calculation, whereby the relation between relative humidity and absolute humidity can be approximately simulated from the partial pressure with a fourth degree polynomial.

It is practical to carry out the calculations in a computer connected to the processing circuit. The same computer can be exploited to process the heat output of the temperature-dependent resistor in order to determine how rapidly the gas is flowing past the instrument. The value can be corrected by way of the simultaneously determined humidity.

One practical field of application for the present invention is medicine. When a patient's breathing is being mechanically mediated for instance, the breathing tube extends through the upper air passages and prevents the nose from exerting its normal climate-regulating function. Since the gases obtained from a central source or from canisters in a hospital situation are practically free of water, appropriate humidifying measures must be taken.

When a breathing gas is humidified with heat-and-moisture exchangers, "artificial noses", the empirical differences in humidity can be exploited as a criterion for differentiating between inhaled and exhaled gas.

Active air-conditioning devices add specific doses of water to the injected air from a reservoir. When such devices are employed, the instrument can be included in a system that regulates the appropriate moisture level. The instrument can alternatively be employed to monitor a manually regulated humidity.

In this case of application, finally, the speed of the gas can also be exploited as a criterion for distinguishing between inhalation and exhalation and hence for revealing the difference between the humidities of the inhaled and exhaled air.

What is claimed is:

1. An instrument for determining the water content of a gas comprising a capacitative sensor for making measurements of an electrical capacity that varies as a function of water content or humidity of the gas, where said capacitative sensor is thermally coupled to a heating element and a temperature probe, a source of energy connected to the heating element, a first signal processing circuit connected to the capacitative sensor, and a second signal-processing circuit connected to the temperature probe, wherein the heating element and the temperature probe comprise a single temperature-dependent resistor, the second signal-processing circuit, the temperature-dependent resistor, and the source of energy comprise a regulating circuit that maintains the temperature of the capacitative sensor constant by automatic control of said heating element, the first signal processing circuit interpolates or extrapolates in accordance with measurements for the capacity of the capacitative sensor a single variable in the form of the actual value of the relative or absolute humidity of the gas obtained from previously determined calibration values at the same constant temperature and/or determines the absolute humidity of the gas from its relative humidity or its relative humidity from its absolute humidity in conjunction with the partial pressure of the water vapor.

2. An instrument as claimed in claim 1, including a flat base of highly heat-conductive ceramic with the capacitative sensor on one side and the temperature-dependent resistor on the other.

3. An instrument as claimed in claim 1, including a thermal insulation wrap that acts as heat insulation and that is discontinuous and moisture-permeable on a side that the capacitative sensor is mounted on.

4. An instrument as claimed in claim 1, wherein the temperature-dependent resistor is accommodated in a measuring bridge having a diagonal, the energy source is a pulse generator connected to the measuring bridge, the second signal-processing circuit includes an input terminal that is connected to the diagonal of the measuring bridge and an output terminal that is connected to a regulator that regulates a pulse-to-pause ratio of the generator.

5. An instrument as claimed in claim 1, wherein the temperature-dependent resistor is included in a measuring bridge having a diagonal, the energy source is a source of direct voltage or direct current, a pulse generator is connected to the measuring bridge and superposes a signal of constant amplitude over the direct voltage or direct current from the energy source, and the second signal-processing circuit demodulates the signal from the pulse generator, the second signal-processing circuit includes an input terminal connected to the diagonal of the measuring bridge and an output terminal connected to a regulator that controls the direct voltage or direct current from the energy source.

6. An instrument as claimed in claim 1, wherein the first signal-processing circuit includes a pulse generator and the capacitative sensor constitutes a timing stage, with either pulse frequency of the pulse generator or a pulse-to-pulse ratio of the pulse generator being measured.

7. An instrument as claimed in claim 4, including a third signal-processing circuit that detects deviations in heat output or performance of the regulator, compares said deviations with previously obtained calibration values, and accordingly determines how rapidly the gas is flowing.

8. An instrument as claimed in claim 7, wherein the third signal processing circuit is coupled with the first signal processing circuit and, as the third signal processing circuit determines how rapidly the gas is flowing, modifies values output by the first signal processing circuit.

9. A method of determining the water content of a gas by means of an instrument that includes a capacitative sensor which makes measurements of an electrical capacity that varies as a function of water content or humidity of the gas, where said capacitative sensor is thermally coupled to a heating element and a temperature probe, the capacitative sensor being maintained at a constant temperature above the condensation point by automatic control of said heating element and a value for relative or absolute humidity is determined from measurements made of the capacity, which depends on the water content, of the capacitative sensor and constructed by interpolation or extrapolation of calibration values previously determined at the same temperature, and/ or the absolute or relative humidity of the gas is determined from its relative or absolute humidity of the gas in conjunction with the partial pressure of the water vapor.

10. A method as claimed in claim 9, wherein a rate of flow of the gas is determined by determining the heat output of the heating element.

11. A method as claimed in claim 10, wherein values representing the rate of flow of the gas are modified by taking empirical values for the humidity into consideration.

12. An instrument as claimed in claim 2, including a thermal insulation wrap that acts as heat insulation and that is discontinuous and moisture-permeable on a side that the capacitative sensor is mounted on.

13. An instrument as claimed in claim 2, wherein the temperature-dependent resistor is accommodated in a measuring bridge, the energy source is a pulse generator connected to the measuring bridge, and the second signal-processing circuit includes an input terminal that is connected to the diagonal of the bridge and an output terminal that is connected to a regulator that regulates a pulse-to-pause ratio of the pulse generator.

14. An instrument as claimed in claim 3, wherein the temperature-dependent resistor is accommodated in a measuring bridge, the energy source is a pulse generator connected to the measuring bridge, and the second signal-processing circuit includes an input terminal that is connected to the diagonal of the measuring bridge and an output terminal that is connected to a regulator that regulates a pulse-to-pause ratio of the pulse generator.

15. An instrument as claimed in claim 12, wherein the temperature-dependent resistor is accommodated in a measuring bridge, the energy source is a pulse generator connected to the measuring bridge, and the second signal-processing circuit includes an input terminal that is connected to the diagonal of the measuring bridge and an output terminal that is connected to a regulator that regulates a pulse-to-pause ratio of the pulse generator.

16. An instrument as claimed in claim 2, wherein the temperature-dependent resistor is included in a measuring bridge having a diagonal, the energy source is a source of direct voltage or direct current, a pulse generator is connected to the measuring bridge and superposes a signal of constant amplitude over the direct voltage or direct current from the energy source, the second signal-processing circuit demodulates the signal from the pulse generator, and the second signal-processing circuit includes an input terminal connected to the diagonal of the measuring bridge and an output terminal connected to a regulator that controls the direct voltage or direct current from the energy source.

17. An instrument as claimed in claim 3, wherein the temperature-dependent resistor is included in a measuring bridge having a diagonal, the energy source is a source of direct voltage or direct current, a pulse generator is connected to the measuring bridge and superposes a signal of constant amplitude over the direct voltage or direct current from the energy source, the second signal-processing circuit demodulates the signal from the pulse generator, and the second signal-processing circuit includes an input terminal connected to the diagonal of the measuring bridge and an output terminal connected to a regulator that controls the direct voltage or direct current from the energy source.

18. An instrument as claimed in claim 12, wherein the temperature-dependent resistor is included in a measuring bridge, the energy source is a source of direct voltage or direct current, a pulse generator is connected to the measuring bridge and superposes a signal of constant amplitude over the direct voltage or direct current from the energy source, the second signal-processing circuit demodulates the signal from the pulse generator, and the second signal-processing circuit includes an input terminal connected to the diagonal of the measuring bridge and an output terminal connected to a regulator that controls the direct voltage or direct current from the energy source.

19. An instrument as claimed in claim 2, wherein the first signal-processing circuit includes a pulse generator and the capacitative sensor constitutes a timing stage, with either pulse frequency of the pulse generator or pulse-to-pause ratio of the pulse generator being measured.

20. An instrument as claimed in claim 5, including a third signal-processing circuit that detects deviations in heat output or performance of the regulator, compares said deviations with previously obtained calibration values, and accordingly determines how rapidly the gas is flowing.

* * * * *